(12) United States Patent
Mukunoki et al.

(10) Patent No.: US 11,261,276 B2
(45) Date of Patent: Mar. 1, 2022

(54) POLYMER, METHOD FOR PRODUCING POLYMER AND POLYMER FLOCCULANT

(71) Applicant: Mitsubishi Chemical Corporation, Chiyoda-ku (JP)

(72) Inventors: Kazunori Mukunoki, Tokyo (JP); Toshiaki Hattori, Tokyo (JP); Shin Suwabe, Tokyo (JP); Yasuharu Mori, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 176 days.

(21) Appl. No.: 16/196,611

(22) Filed: Nov. 20, 2018

(65) Prior Publication Data

US 2019/0085105 A1    Mar. 21, 2019

Related U.S. Application Data

(63) Continuation of application No. PCT/JP2017/020033, filed on May 30, 2017.

(30) Foreign Application Priority Data

May 31, 2016 (JP) .............................. JP2016-108201

(51) Int. Cl.

| | |
|---|---|
| *C08F 220/34* | (2006.01) |
| *D21H 21/18* | (2006.01) |
| *D21H 17/45* | (2006.01) |
| *C07C 209/06* | (2006.01) |
| *B01D 21/01* | (2006.01) |
| *C08F 220/56* | (2006.01) |
| *D21H 21/10* | (2006.01) |
| *C08F 220/40* | (2006.01) |
| *C08F 20/34* | (2006.01) |
| *C02F 1/56* | (2006.01) |
| *C08F 20/12* | (2006.01) |
| *C08F 20/56* | (2006.01) |
| *C02F 103/28* | (2006.01) |
| *C08F 2/38* | (2006.01) |
| *C08K 5/09* | (2006.01) |

(52) U.S. Cl.
CPC ............ *C08F 220/34* (2013.01); *B01D 21/01* (2013.01); *C02F 1/56* (2013.01); *C07C 209/06* (2013.01); *C08F 20/12* (2013.01); *C08F 20/34* (2013.01); *C08F 20/56* (2013.01); *C08F 220/40* (2013.01); *C08F 220/56* (2013.01); *D21H 17/45* (2013.01); *D21H 21/10* (2013.01); *D21H 21/18* (2013.01); *C02F 2103/28* (2013.01); *C08F 2/38* (2013.01); *C08F 2810/20* (2013.01); *C08K 5/09* (2013.01); *D21H 17/455* (2013.01)

(58) Field of Classification Search
CPC ...... C08F 20/34; C08F 220/34; C08F 220/40; C08F 20/40; C02F 1/56; B01D 21/01; D21H 17/45; D21H 17/455
See application file for complete search history.

(56) References Cited

U.S. PATENT DOCUMENTS

| | | | | |
|---|---|---|---|---|
| 3,278,474 A | * | 10/1966 | Nixon ...................... | C08G 2/18 |
| | | | | 524/814 |
| 3,689,468 A | * | 9/1972 | Cenci et al. ........... | G03G 5/107 |
| | | | | 526/312 |

(Continued)

FOREIGN PATENT DOCUMENTS

| | | |
|---|---|---|
| EP | 2 339 401 A1 | 6/2011 |
| GB | 1438719 | 6/1976 |

(Continued)

OTHER PUBLICATIONS

Combined Chinese Office Action and Search Report dated Jun. 15, 2020 in Patent Application No. 201780032246.9 (with unedited computer generated English translation), 13 pages.

(Continued)

*Primary Examiner* — Ling Siu Choi
*Assistant Examiner* — David L Miller
(74) *Attorney, Agent, or Firm* — Oblon, McClelland, Maier & Neustadt, L.L.P.

(57) ABSTRACT

Provided is a polymer flocculant which is capable of controlling the structure of a polymer that is a copolymerization product of a monomer (a) having a structure derived from formula (I) in each molecule and a water-soluble unsaturated monomer (b) having a polymerizable unsaturated bond in each molecule, and which has a branched or cross-linking structure, and is excellent in water-solubility and water dispersibility,

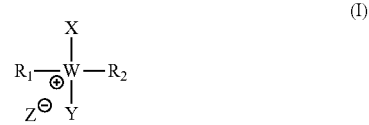

(I)

In formula (I), $R_1$ and $R_2$ are respectively a linear or branched functional group configured of atoms selected from the group consisting of carbon not having a carbon-carbon unsaturated bond, oxygen, nitrogen, and hydrogen; W is a non-metal element of the group 15; X and Y are each a linear or branched functional group configured of atoms selected from the group consisting of carbon, oxygen, nitrogen, and hydrogen, and each have at least one carbon-carbon unsaturated bond, provided that X and Y have different structures; and Z is a chlorine ion, a bromine ion, or an iodine ion.

19 Claims, No Drawings

(56) References Cited

U.S. PATENT DOCUMENTS

| | | |
|---|---|---|
| 3,975,341 A | 8/1976 | Trapasso |
| 4,681,929 A | 7/1987 | Cole et al. |
| 4,717,758 A | 1/1988 | Ogawa et al. |
| 4,720,346 A | 1/1988 | Flesher et al. |
| 5,252,103 A | 10/1993 | Kamata et al. |
| 2004/0087717 A1 | 5/2004 | Peltier et al. |
| 2004/0192840 A1 | 9/2004 | Peltier et al. |
| 2006/0084772 A1 | 4/2006 | Wong Shing et al. |
| 2008/0064819 A1 | 3/2008 | Wright |
| 2010/0197853 A1 | 8/2010 | Sugaya |

FOREIGN PATENT DOCUMENTS

| | | |
|---|---|---|
| JP | 49-64689 | 6/1974 |
| JP | 59-1247 | 1/1984 |
| JP | 61-293509 | 12/1986 |
| JP | 4-263678 | 9/1992 |
| JP | 2004-255378 | 9/2004 |
| JP | 2010-502800 | 1/2010 |
| JP | 2011-154367 | 8/2011 |
| WO | WO 2009/008260 A1 | 1/2009 |

OTHER PUBLICATIONS

International Search Report dated Aug. 1, 2017 in PCT/JP2017/020033, filed on May 30, 2017 (with English Translation).
Canadian Office Action dated Nov. 22, 2019 in Patent Application No. 3,025,126, 3 pages.
Extended European Search Report dated Apr. 17, 2019 in European Patent Application No. 17806659.3, 5 pages.
Office Action dated Sep. 3, 2019 in corresponding Japanese Patent Application No. 2018-520917 (with English Translation), 6 pages.

* cited by examiner

POLYMER, METHOD FOR PRODUCING POLYMER AND POLYMER FLOCCULANT

TECHNICAL FIELD

The present invention relates to a polymer using a polyfunctional monomer. Specifically, the invention relates to polyfunctional monomers having different reactivities, a polymer structure-controlled by using the polyfunctional monomer, and a polymer flocculant using the polymer.

This application claims priority based on Japanese Patent Application No. 2016-filed on May 31, 2016, and the contents thereof are incorporated herein.

BACKGROUND ART

A water-soluble polymer has been widely used in the field of a thickener for petroleum recovery, a polymer flocculant, a papermaking additive, and the like. In particular, a polymer of a water-soluble monomer, such as (meth)acrylamide, has been widely used. In such polymers, the physical properties or the form is adjusted according to an application or a necessary function. The adjustment of a molecular weight or a molecular weight distribution according to an initiator or a chain transfer agent, the adjustment of ionicity according to the introduction of a monomer having an ion group, the introduction of groups having different hydrophilicity or hydrophobicity, such as a benzyl group, the adjustment of random, block, graft, or the like of the monomer according to a polymerization method, the selection of a polymerization method such as aqueous solution polymerization, suspension polymerization, and emulsification polymerization, and the like, are performed as an adjustment method.

Meanwhile, the structure of the polymer is also variously controlled. A linear, branched, or cross-linking structure, is adjusted, and thus, the spreading of molecules in a solution or an aqueous solution viscosity can be controlled, and the functions or the like can be adjusted according to the application.

However, recently, in a case where the water-soluble polymer is used as the polymer flocculant, in the dehydration of organic sludge, a demand for increasing the rate of a dehydrating process has increased due to an increase in a sludge amount to be generated, and thus, a polymer flocculant forming a higher flock strength has been desired. In addition, a polymer flocculant which is capable of realizing a reduction in a moisture content in a dehydrated cake, has been desired due to a steep increase in an incineration cost at the time of incinerating the dehydrated cake, and a tight situation of a landfill at the time of landfilling the dehydrated cake as it is. A branched or cross-linking polymer obtained by controlling the structure of the polymer described above, is proposed as a polymer flocculant exhibiting such flocculation performance.

For example, in Patent Literature 1, it is described that a mesh-like polymer is sheared, and thus, can be used as a flocculant. In Patent Literature 2, it is described that a partially cross-linking polymer is subjected to emulsification polymerization, and thus, can be used as a flocculant. In addition, a method using microemulsion (Patent Literature 3) or the like is also described. Further, a plurality of cross-linking control technologies according to a living polymerization method are reported. In addition, a cross-linking agent used in the related art, has two or more vinyl groups or allyl groups (Patent Literature 4). Further, a method of synthesizing a branched or cross-linking polymer obtained by drawing out a proton in a polymer main chain, and by generating a radical in molecules (Patent Literature 5), by using hydrogen peroxide or the like at the time of performing polymerization, is also proposed. In addition, for example, in Patent Literature 5, a compound having a vinyl group and an allyl group is described.

CITATION LIST

Patent Literature

Patent Literature 1: JP 61-293509 A
Patent Literature 2: JP 49-064689 A
Patent Literature 3: U.S. Pat. No. 4,681,929
Patent Literature 4: JP 2004-255378 A
Patent Literature 5: JP 2011-154367 A

SUMMARY OF THE INVENTION

Problem to be Solved by the Invention

However, in the methods described in Patent Literatures 1 to 3, only the cross-linking agent is simply used, a water-insoluble swollen gel having a three-dimensional network structure tend to be obtained, and it is difficult to produce a water-soluble or water dispersible polymer having a controlled suitable branched chain. In addition, in the polymer flocculant described in Patent Literature 4, the functional group's reactivities of the cross-linking agents to be used are the same, and the reactivity is also low, and thus, sufficient performance is not obtainable. Further, in Patent Literature 5, in the compound having a vinyl group and an allyl group, there is no example of being used for producing or structure-controlling a water-soluble polymer such as a flocculant.

An object of the invention is to provide a polymer which is capable of generating a coarse flock, is capable of controlling the structure of the polymer by a general aqueous solution polymerization method, and is suitable for an application of a polymer flocculant or the like, excellent in water solubility and water dispersibility, with a branched or cross-linking structure.

Means for Solving Problem

The present inventors have obtained the following conclusion, as a result of intensive studies in consideration of the circumstances described above.

[1] A polymer which is a copolymer of a cross-linkable monomer (a) having a structure derived from Formula (I) in the molecule, and a water-soluble unsaturated monomer (b) having a polymerizable unsaturated bond in the molecule

[Chem. 1]

(I)

$R_1$ and $R_2$ are respectively a linear or branched functional group configured of atoms selected from the group consisting of carbon not having a carbon-carbon unsaturated bond, oxygen, nitrogen, and hydrogen, W is a non-metal element of the group 15, X and Y are each a linear or branched functional group configured of atoms selected from the group consisting of carbon, oxygen, nitrogen, and hydrogen, and each have at least one carbon-carbon unsaturated bond, provided that X and Y have different structures, and Z is a chlorine ion, a bromine ion, or an iodine ion.

[2] The polymer according to [1] described above, in which when a viscosity is measured by a rotatory viscometer, in a state of an aqueous solution of 0.5 mass %, the viscosity is greater than or equal to 5 mPa·s and less than or equal to 10000 mPa·s at 25° C.

[3] The polymer according to [1] described above, in which X and Y have structures described below,

[Chem. 2]

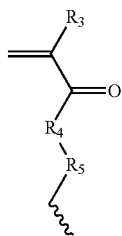

(X)

in the formula, $R_3$ is a hydrogen atom or a methyl group, $R_4$ is O or NH, and $R_5$ is $C_nH_{2n}$ (n=1 to 6).

[Chem. 3]

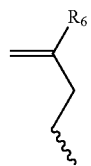

(Y)

in the formula, $R_6$ is a hydrogen atom, a methyl group, or an alkyl ester group having a linear, branched, or cyclic structure of 1 to 6 carbon atoms.

[4] The polymer according to [1] described above, in which the structure derived from Formula (I) is Formula (II) described below,

[Chem. 4]

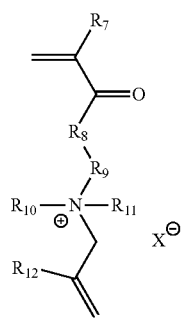

(II)

in the formula, $R_{10}$ and $R_{11}$ are each independently a linear or branched alkyl group having 1 to 6 carbon atoms, $R_7$ is a hydrogen atom or a methyl group, $R_8$ is O or NH, $R_9$ is $C_nH_{2n}$ (n=1 to 6), and $R_{12}$ is an hydrogen atom, a methyl group, or an alkyl ester group having a linear, branched, or cyclic structure of 1 to 6 carbon atoms.

[5] A polymer flocculant, containing: the polymer according to any one of [1] to [4].

[6] A paper strengthening agent, containing: the polymer according to any one of [1] to [4].

[7] A method for producing a polymer flocculant, comprising:

dissolving a cross-linkable monomer (a) having a structure derived from Formula (I) in the molecule, and a water-soluble unsaturated monomer (b) having a polymerizable unsaturated bond in the molecule, in water; and polymerizing the cross-linkable monomer (a) and the water-soluble unsaturated monomer (b) dissolved in water in a homogeneous system,

[Chem. 5]

(I)

$R_1$ and $R_2$ are respectively a linear or branched functional group configured of atoms selected from the group consisting of carbon not having a carbon-carbon unsaturated bond, oxygen, nitrogen, and hydrogen, W is a non-metal element of the group 15, X and Y are each a linear or branched functional group configured of atoms selected from the group consisting of carbon, oxygen, nitrogen, and hydrogen, and each have at least one carbon-carbon unsaturated bond, provided that X and Y have different structures, and Z is a chlorine ion, a bromine ion, or an iodine ion.

Effect of the Invention

The polymer of the invention, for example, is added and mixed to sewage sludge or wastewater in the case of being used as a polymer flocculant, and thus, a coarse flock is formed. Further, a water-soluble and water dispersible polymer having a branched or cross-linking structure is obtained even in a homogeneous aqueous solution system, and thus, the polymer of the invention is suitable for producing a polymer flocculant or a papermaking agent at a low cost.

Mode(s) for Carrying Out the Invention

Hereinafter, the details of the invention will be described.

A polymer containing a cross-linking agent, which is used in the invention, is a polymer obtained by copolymerizing a monomer (a) having a structure derived from Formula (I) described below in molecules, and a water-soluble unsaturated monomer (b) having a polymerizable unsaturated bond in molecules.

[Chem. 6]

(I)

$R_1$ and $R_2$ are respectively a linear or branched functional group configured of atoms selected from the group consisting of carbon not having a carbon-carbon unsaturated bond, oxygen, nitrogen, and hydrogen, W is a non-metal element of the group 15, X and Y are each a linear or branched functional group configured of atoms selected from the group consisting of carbon, oxygen, nitrogen, and hydrogen, and each have at least one carbon-carbon unsaturated bond, provided that X and Y have different structures, and Z is a chlorine ion, a bromine ion, or an iodine ion.

[Chem. 7]

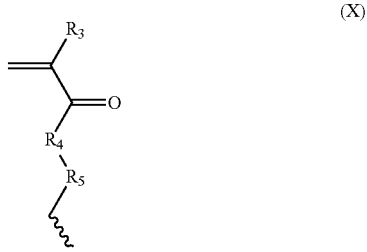
(X)

Here, $R_3$ is a hydrogen atom or a methyl group, $R_4$ is O or NH, and $R_5$ is $C_nH_{2n}$ (n=1 to 6).

Examples of the chain functional group not having a carbon-carbon unsaturated bond include a methyl group, an ethyl group, a propyl group, an i-propyl group, an n-butyl group, an i-butyl group, and a carbonyl group.

W is a non-metal element of group 15, and examples thereof include nitrogen, phosphorus, arsenic, antimony, and bismuth.

Examples of the chain functional group having at least one carbon-carbon unsaturated bond include a (meth)acryloyl group, a crotonoyl group, and a vinyl ether group.

For example, a structure having a (meth)acryl group in which $R_3$ is a hydrogen atom, and $R_4$ is O, in Formula (X), and a (meth)acrylamide group in which $R_3$ is a hydrogen atom, and $R_4$ is NH, in Formula (X), is preferable.

A structure having a (meth)acryl group or a (meth)acrylamide group, is excellent in copolymerizability with respect to the water-soluble unsaturated monomer (b).

[Chem. 8]

(Y)

Here, $R_6$ is a hydrogen atom, a methyl group, or an alkyl ester group having a linear, branched, or cyclic structure of 1 to 6 carbon atoms.

In the cross-linkable monomer (a), X and Y have different structures, and thus, X and Y have different polymerizability.

For example, in methylene bisacrylamide, diallyl amine, triallyl amine, and the like, a molecular structure is symmetric, and polymerizability of the functional group is the same, and thus, the extension and the cross-linkage of the main chain simultaneously occur, and it is difficult to control the structure.

In contrast, in the case of using the cross-linkable monomer (a), which is used in the invention, there is a difference in the reactivity between the extension and branching cross-linkage of the main chain, and thus, the structure is extremely easily controlled, and as a result thereof, a branched structure is obtained even in a homogeneous aqueous solution system, and a water-soluble polymer can be easily produced.

Further, the branched polymer has a low aqueous solution viscosity compared to the molecular weight, and has excellent handleability. It is necessary that the polymer flocculant is rapidly mixed to polluted water or sludge, and thus, a branched polymer aqueous solution is more easily used than a highly viscous linear polymer aqueous solution. In addition, in other branching cross-linking polymer flocculants, there are some cases where gelled substances, which are not homogeneous and have poor solubility, remain, but in the invention, a branching effect can be obtained, and a polymer with less insolubilized material can be easily obtained.

In the invention, it is preferable that the structure derived from Formula (I) is Formula (II) described below.

[Chem. 9]

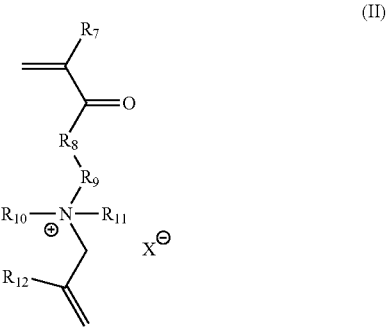
(II)

Here, $R_{10}$ and $R_{11}$ are each independently a linear or branched alkyl group having 1 to 6 carbon atoms, $R_7$ is a hydrogen atom or a methyl group, $R_8$ is O or NH, $R_9$ is $C_nH_{2n}$ (n=1 to 6), and $R_{12}$ is a hydrogen atom, a methyl group, or an alkyl ester group having a linear, branched, or cyclic structure of 1 to 6 carbon atoms.

The structure derived from Formula (I) is Formula (II), and thus, reactivity difference appears remarkably, and a branching/cross-linking degree is easily controlled.

Each monomer represented by Formulas (III-1) to (III-12) described below, can be exemplified as the cross-linkable monomer (a) of the invention. Such monomers may be independently used, or two or more types thereof may be used together.

[Chem. 10]

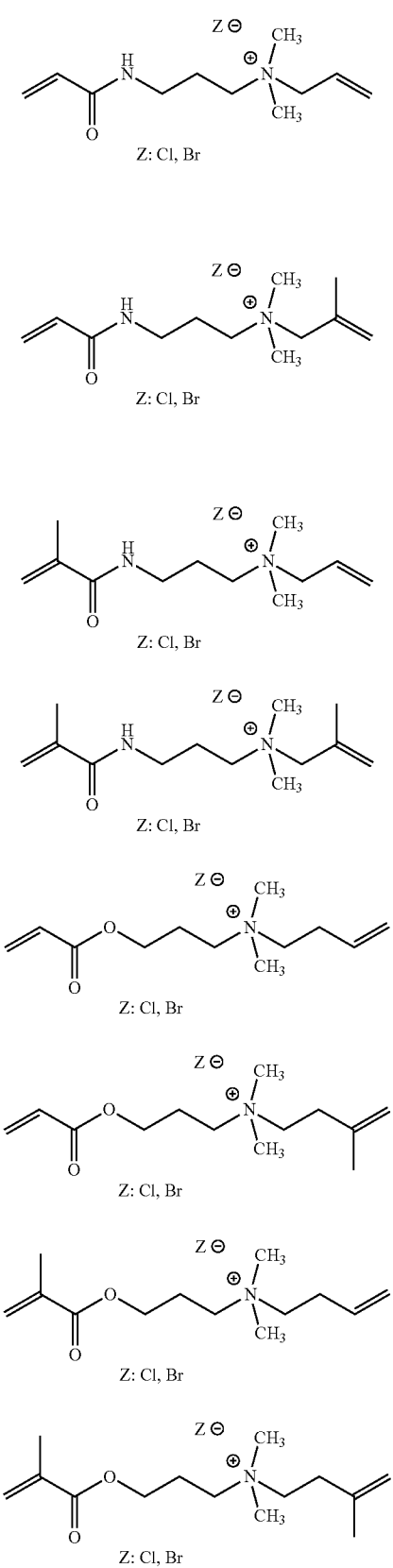

(III-1) 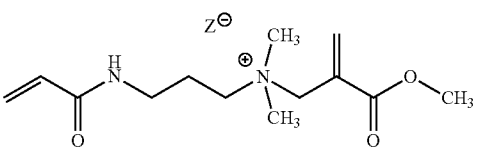

(III-9) 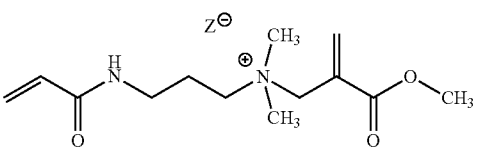

(III-2) 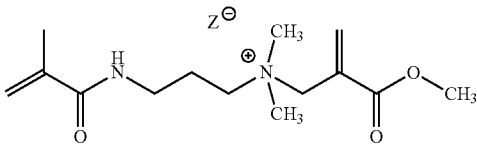

(III-10) 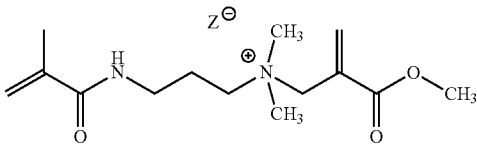

(III-3)

(III-11) 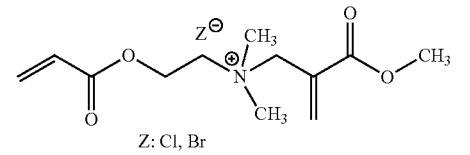

(III-4)

(III-12) 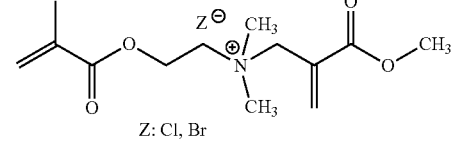

(III-5)

(III-6)

(III-7)

(III-8)

A method for producing the cross-linkable monomer (a) of the invention is not particularly limited, but for example, the following method can be exemplified.

First, a solution (A) in which tertiary amine having a polymerizable unsaturated bond is dissolved in an organic solvent, and a solution (B) in which a halogenide having a polymerizable unsaturated bond is dissolved in an organic solvent, are prepared, respectively. Next, the solution (B) is dropped into a beaker by using a dropping funnel, in a state where the solution (A) is stirred in the beaker, and is continuously stirred as it is. At this time, a stirring time or the temperature of the beaker at the time of dropping may be arbitrarily set.

An added amount of the cross-linkable monomer (a) is preferably greater than or equal to 0.001 mass % and less than or equal to 1.0 mass %, is more preferably greater than or equal to 0.003 mass % and less than or equal to 0.7 mass %, and is particularly preferably greater than or equal to 0.005 mass % and less than or equal to 0.5 mass %, with respect to 100 mass % of the water-soluble unsaturated monomer (b), from the viewpoint of flocculation performance (a high flock strength, a coarse flock, and a low moisture content of a dehydrated cake) and the solubility of the polymer to be obtained with respect to water.

The water-soluble unsaturated monomer (b) of the invention indicates an unsaturated monomer of which a solubility with respect to 100 g of water (20° C.) is greater than or equal to 5 g, and includes the followings.

(b1) Nonionic Monomer (b1-1) to (b1-3) described below, and mixtures thereof are exemplified.

(b1-1) Hydroxyl Group or Nitrile Group-Containing (Meth)Acrylate

For example, a hydroxyl group-containing compound having 5 to 25 carbon atoms [specifically, hydroxy ethyl (meth)acrylate, diethylene glycol mono(meth)acrylate, polyethylene glycol mono(meth)acrylate, polyglycerol mono(meth)acrylate, and the like], or a nitrile group-containing compound [2-cyanoethyl (meth)acrylate and the like] are exemplified.

(b1-2) (Meth)Acrylamide Compound

For example, (meth)acrylamide [N-alkyl (meth)acrylamide, N-methyl (meth)acrylamide, ethyl (meth)acrylamide, and isopropyl (meth)acrylamide, N,N-dimethyl (meth)acrylamide, diethyl (meth)acrylamide, and diisopropyl (meth)acrylamide] and N-alkylol, and (meth)acrylamide [N-methylol (meth)acrylamide, N,N-dimethylol (meth)acrylamide, and the like] are exemplified.

(b1-3) Nitrogen Atom-Containing Vinyl Monomer Other than (b1-1) and (b1-2)

For example, acrylonitrile, N-vinyl formamide, N-vinyl-2-pyrrolidone, vinyl imidazole, N-vinyl succinimide, N-vinyl carbazole, and the like are exemplified.

(b2) Cationic Monomer (b2-1) to (b2-5) described below, and salts thereof can be exemplified. For example, a salt of an inorganic acid (a hydrochloric acid, a sulfuric acid, a phosphoric acid, a nitric acid, and the like), and a quaternary ammonium salt (for example, a methyl chloride salt, a dimethyl sulfuric acid salt, a benzyl chloride salt, and mixtures thereof) are exemplified as the salt.

(b2-1) Tertiary Amino Group-Containing (Meth)Acrylate

For example, N,N-dialkyl aminoalkyl (meth)acrylate [specifically, N,N-dimethyl aminoethyl (meth)acrylate, N,N-dimethyl aminopropyl (meth)acrylate, N,N-diethyl aminoethyl (meth)acrylate, N,N-diethyl aminopropyl (meth)acrylate, and the like], and N-morpholinoalkyl (meth)acrylate such as N-morpholinoethyl (meth)acrylate, are exemplified.

(b2-2) Tertiary Amino Group-Containing (Meth)Acrylamide Compound

For example, N,N-dialkyl aminoalkyl (meth)acrylamide [specifically, N,N-dimethyl aminoethyl (meth)acrylamide, N,N-dimethyl aminopropyl (meth)acrylamide, N,N-diethyl aminoethyl (meth)acrylamide, N,N-diethyl aminopropyl (meth)acrylamide, and the like], and N-morpholinoalkyl (meth)acrylamide such as N-morpholinoethyl (meth)acrylamide, are exemplified.

(b2-3) Vinyl Compound Having Primary or Secondary Amino Group

For example, a vinyl compound having an amino group of 3 to 12 carbon atoms, such as vinyl aniline, allyl amine, and N-methyl vinyl amine, is exemplified.

(b2-4) Compound Having Amine Imide Group

For example, 1,1,1-trimethyl amine (meth)acrylimide, 1,1-dimethyl-1-ethyl amine (meth)acrylimide, 1,1-dimethyl-1-(2'-phenyl-2'-hydroxyethyl)amine (meth)acrylimide, and 1,1,1-trimethyl amine (meth)acrylimide are exemplified.

(b2-5) Nitrogen Atom-Containing Vinyl Compound Other than (b2-1) to (b2-4)

For example, 2-vinyl pyridine, 3-vinyl piperidine, vinyl pyrazine, vinyl morpholine, and the like are exemplified.

(b3) Anionic Monomer

For example, a salt of an alkali metal (lithium, sodium, potassium, and the like) or an alkali earth metal (magnesium, calcium, and the like), an ammonium salt, and amines having 1 to 20 carbon atoms, and mixtures thereof are exemplified.

(b3-1) Unsaturated Carboxylic Acid (Also Including Anhydride)

For example, a monocarboxylic acid such as a (meth)acrylic acid, a vinyl benzoic acid, or an allyl acetic acid, and a dicarboxylic acid such as a di(anhydride)maleic acid, a fumaric acid, or an itaconic acid are exemplified.

(b3-2) Unsaturated Sulfonic Acid

For example, unsaturated hydrocarbon having a sulfonic acid group, such as a vinyl sulfonic acid and a styrene sulfonic acid; (meth)acrylate having a sulfonic acid group, such as a 2-(meth)acryloyloxyethane sulfonic acid, a 2-(meth)acryloyloxypropane sulfonic acid, a 3-(meth)acryloyloxypropane sulfonic acid, a 2-(meth)acryloyloxybutane sulfonic acid, a 4-(meth)acryloyloxybutane sulfonic acid, a 2-(meth)acryloyloxy-2,2-dimethyl ethane sulfonic acid, or a p-(meth)acryloyloxymethyl benzene sulfonic acid; (meth)acrylamide having a sulfonic acid group, such as a 2-(meth)acryloyl aminoethane sulfonic acid, a 2-(meth)acryloyl aminopropane sulfonic acid, a 3-(meth)acryloyl aminopropane sulfonic acid, a 2-(meth)acryloyl aminobutane sulfonic acid, a 4-(meth)acryloyl aminobutane sulfonic acid, a 2-(meth)acryloyl amino-2,2-dimethyl ethane sulfonic acid, and a p-(meth)acryloyl aminomethyl benzene sulfonic acid; (meth)allyl sulfosuccinate having 5 to 20 carbon atoms, and the like are exemplified.

In (b) described above, the sulfonic acid group-containing (meth)acrylate and the sulfonic acid group-containing (meth)acrylamide in (b1-1), (b2-1), (b2-2), (b3-1), and (b3-2) are preferable, and the (meth)acrylamide in (b1-2), the acrylonitrile and the N-vinyl formamide in (b1-3), the N,N-dimethyl aminoethyl (meth)acrylate and the salts thereof in (b2-1), the (meth)acrylic acid, the (anhydride)maleic acid, the itaconic acid, and the salts of the alkali metal (lithium, sodium, potassium, and the like) in (b3-1), and the 2-(meth)acryloyloxyethane sulfonic acid, the 2-(meth)acryloyloxypropane sulfonic acid, the 3-(meth)acryloyloxypropane sulfonic acid, the 2-(meth)acryloyl amino-2,2-dimethyl ethane sulfonic acid and the alkali metal salts thereof in (b3-2), are most preferable, from the viewpoint of having a higher molecular weight.

In addition, such (b) may be independently polymerized, or may be arbitrarily copolymerized.

In (b) described above, other monomers (x) may be used together as necessary, and in this case, a ratio (mol %) of (x) is generally greater than or equal to 0, is preferably greater than or equal to 0.1, and is more preferably greater than or equal to 0.5, and is generally less than or equal to 40, is preferably less than or equal to 20, and is more preferably less than or equal to 10, with respect to the total number of moles of the monomer (b) and (x).

Here, the other monomers indicate a monomer of which a solubility with respect to 100 g of water (20° C.) is less than 5 g.

Examples of the other monomers (x) include the followings.

(x1) to (x5) Described below, and Mixtures thereof (x1) (Meth)Acrylate Having 4 to 23 Carbon Atoms For example, epoxy group-containing (meth)acrylate having 6 to 20 carbon atoms, such as methyl (meth)acrylate, ethyl (meth)acrylate, butyl (meth)acrylate, octadecyl (meth)acrylate, cyclohexyl (meth)acrylate, and glycidyl (meth)acrylate, is exemplified.

(x2) Polypropylene Glycol

For example, an adduct of propylene oxide (hereinafter, simply referred to as PO) of unsaturated carboxylic acid monoester monool or diol, is exemplified. Specifically, (meth)acrylic acid ester [ω-methoxy propylene oxide, ethoxy propylene oxide, propoxy propylene oxide, butoxy propylene oxide, cyclohexoxy propylene oxide, and phenoxy polypropylene glycol (meth)acrylate], and the like, in which monool (ethanol, propanol, butanol, and the like) is added to PO, are considered.

(x3) Unsaturated Hydrocarbon

For example, unsaturated hydrocarbon having 2 to 30 carbon atoms, such as ethylene, nonene, styrene, and 1-methyl styrene, is exemplified.

(x4) Unsaturated Alcohol

For example, unsaturated alcohol having 3 to 20 carbon atoms, such as vinyl alcohol and (meth)allyl alcohol, and alcohol-derived ester thereof, such as vinyl acetate, are exemplified.

(x5) Halogen-Containing Compound

For example, vinyl chloride, vinyl bromide, and the like are exemplified.

A polymerization method of the invention is not particularly limited, but for example, bulk polymerization, aqueous solution polymerization, precipitation polymerization, suspension polymerization, emulsification polymerization, and microemulsion polymerization, and the like are exemplified as the polymerization method. Among them, it is preferable that the polymerization is performed in an aqueous solution system, from the viewpoint of most simply performing the polymerization at a low cost.

In the polymerization method of the invention, first, the cross-linkable monomer (a) and the water-soluble unsaturated monomer (b) are dissolved in water. Next, a polymerization initiator, and a chain transfer agent or the like, as necessary, are added, and then, nitrogen gas is blown, and thus, a reactive monomer solution is obtained. The reactive monomer solution is subjected to thermal polymerization by using a water bath, in a case where the added polymerization initiator is a thermal polymerization initiator, and is subjected to photopolymerization by using UV or a chemical lamp, in a case where the added polymerization initiator is a photopolymerization initiator.

By performing the polymerization method of the invention, it is possible to simply perform the polymerization at a low cost.

In addition, polymerization using a general radical initiator, is used, and a general azo-based initiator or a peroxide-based initiator, a photopolymerization initiator using a photosensitizer, a redox initiator, and the like are exemplified as the radical initiator. The azo-based initiator or the peroxide-based initiator, the photopolymerization initiator using the photosensitizer, the redox initiator, and the like may be independently used, or may be used together.

Examples of the azo-based initiator or the peroxide-based initiator include 1,1'-azobis(cyclohexane-1-carbonitrile), 2,2'-azobis(2,4,4-trimethyl pentene), 2-cyano-2-propylazo-formamide, dicumyl peroxide, t-butyl cumyl peroxide, di-t-butyl peroxide, t-butyl peroxy-3,3,5-trimethyl hexanoate, t-butyl peroxylaurate, t-butyl peroxyacetate, di-t-butyl peroxyhexahydroterephthalate, di-t-butyl peroxyazelate, t-butyl peroxyallyl carbonate, t-butyl peroxyisopropyl carbonate, 1,1-di-t-butyl peroxycyclohexane, 1,1-di-t-butyl peroxy-3,3,5-trimethyl cyclohexane, 1,1-di-t-hexyl peroxy-3,3,5-trimethyl cyclohexane, 2,2'-azobis(2,4-dimethyl-4-methoxy valeronitrile), 2,2'-azobis(2,4-dimethyl valeronitrile), 2,2'-azobisisobutyronitrile, 2,2'-azobis(2-methyl butyronitrile), acetyl cyclohexyl sulfonyl peroxide, isobutyryl peroxide, cumyl peroxyneodecanoate, di-isopropyl peroxycarbonate, di-allyl peroxydicarbonate, di-n-propyl peroxydicarbonate, di-myristyl peroxydicarbonate, cumyl peroxyneohexanoate, di(2-ethoxy ethyl) peroxydicarbonate, di(methoxy isopropyl) peroxydicarbonate, di(2-ethyl hexyl)peroxydicarbonate, t-hexyl peroxyneodecanate, di(3-methyl-3-methoxy butyl) peroxydicarbonate, t-butyl peroxyneodecanoate, t-hexyl peroxyneohexanoate, t-butyl peroxyneohexanoate, 2,4-dichlorobenzoyl peroxide, t-hexyl peroxypivalate, t-butyl peroxypivalate, 3,5,5-trimethyl hexanoyl peroxide, octanoyl peroxide, decanoyl peroxide, lauroyl peroxide, cumyl peroxyoctoate, and acetyl peroxide. These can be used together.

Examples of the photopolymerization initiator include a carbonyl compound such as benzoin, benzoin methyl ether, benzoin ethyl ether, benzoin isopropyl ether, benzoin isobutyl ether, benzyl, benzophenone, p-methoxy benzophenone, 2,2-diethoxy acetophenone, α,α-dimethoxy-α-phenyl acetophenone, methyl phenyl glyoxylate, ethyl phenyl glyoxylate, 4,4'-bis(dimethyl amino)benzophenone, and 2-hydroxy-2-methyl-1-phenyl propan-1-one; a sulfur compound such as tetramethyl thiuram monosulfide and tetramethyl thiuram disulfide; 2,4,6-trimethyl benzoyl diphenyl phosphine oxide, and benzoyl diethoxy phosphine oxide. These can be used together.

Examples of the redox-based initiator include hydrogen peroxide/ferrous salt, persulfate/acidic sodium sulfite, cumene hydroperoxide/ferrous salt, benzoyl peroxide/dimethyl aniline, peroxide (hydrogen peroxide, hydroperoxide, and the like)/organic metal alkyl (triethyl ammonium, triethyl boron, diethyl zinc, and the like), and oxygen/organic metal alkyl.

An added amount of the polymerization initiator is preferably greater than or equal to 0.0001 mass % and less than or equal to 0.05 mass %, is more preferably greater than or equal to 0.0005 mass % and less than or equal to 0.02 mass %, and is particularly preferably greater than or equal to 0.001 mass % and less than or equal to 0.01 mass %, on the basis of the total weight of (a), (b), and (x) as necessary, from the viewpoint of obtaining the optimal molecular weight as the flocculant, the paper strengthening agent, or the like of the invention.

In addition, the chain transfer agent may be used as necessary. The chain transfer agent is not particularly limited, but for example, an organic acid [a 4-pentenoic acid, a 5-hexenoic acid, a 6-heptenoic acid, a 7-octenoic acid, a 8-nonenoic acid, a 9-decenoic acid, a 10-undecenoic acid, a 11-dodecenoic acid, a p-vinyl benzoic acid, a p-allyl benzoic acid, a 3-vinyl phenyl acetic acid, a 4-vinyl phenyl acetic acid, and a 4-allyl phenyl acetic acid], an inorganic acid [a sulfuric acid, a *sulphurous* acid, a nitric acid, a nitrous acid, a phosphoric acid, a phosphorous acid, a diphosphorous acid, and a phosphonic acid], a compound having one or two or more hydroxyl groups in molecules [for example, methanol, ethanol, isopropyl alcohol, ethylene glycol, propylene glycol, polyethylene glycol, and a polyoxyethylene-polyoxypropylene copolymer], a compound having one or two or more amino groups in molecules [for example, ammonia, amine (for example, methyl amine, dimethyl amine, triethyl amine, propanol amine, ethylene diamine, and polyethylene imine], a compound having one or two or more thiol groups in molecules, and the like are exemplified as the chain transfer agent.

A used amount in the case of using the chain transfer agent is preferably greater than or equal to 0.0001 mass % and less than or equal to 0.05 mass %, is more preferably greater than or equal to 0.0005 mass % and less than or equal to 0.02 mass %, and is particularly preferably greater than or equal to 0.001 mass % and less than or equal to 0.01 mass %, on the basis of the total weight of (a), (b), and (x), from the viewpoint of obtaining the optimal molecular weight of the polymer flocculant, the paper strengthening agent, or the like of the invention.

Further, a living radical polymerization method may be used together. The living radical polymerization method is not particularly limited, but for example, a method using a nitroxide compound, a method using a transition metal complex, a method using an additive cleavage chain transfer agent, and the like are exemplified as the living radical polymerization method.

In the aqueous solution polymerization, a monomer concentration in a monomer aqueous solution at the time of performing the polymerization, is preferably greater than or equal to 20 mass % and less than or equal to 80 mass %, is more preferably greater than or equal to 25 mass % and less than or equal to 75 mass %, and is particularly preferably greater than or equal to 30 mass % and less than or equal to 70 mass %, on the basis of the mass of the monomer aqueous solution.

The obtained polymer may be used in a state of an aqueous solution, or may be used by being diluted, and the obtained polymer is powdered once, and then, can be an aqueous solution at the time of being used.

In a case where the polymer is in the state of the aqueous solution, the viscosity of the polymer, which is measured at 25° C. by a rotatory viscometer, is preferably greater than or equal to 5 mPa·s and less than or equal to 10000 mPa·s, is more preferably greater than or equal to 10 mPa·s and less than or equal to 9000 mPa·s, and is even more preferably greater than or equal to 15 mPa·s and less than or equal to 8000 mPa·s.

In a case where the viscosity of the polymer is greater than or equal to 5 mPa·s and less than or equal to 10000 mPa·s, a coarse and solid flock of which the affinity with respect to the sludge is high, can be formed, for example, in the case of being used as a polymer flocculant.

EXAMPLES

Hereinafter, the invention will be described in detail by examples, but the invention is not limited thereto. Furthermore, in the examples, "%" indicates mass %, unless otherwise noted.

First, the invention will be described in detail by the examples, as a flocculant application.

Furthermore, in examples and comparative examples, measured values of a 0.5% viscosity, a 0.5% salt viscosity, and a 0.5% insoluble content of a polymer flocculant, were obtained by performing measurement with respect to a powder-like polymer flocculant, according to the following method.

(Measurement of 0.5% Viscosity)

2.5 g of a sample was dissolved in water, and thus, 500 g of a polymer aqueous solution of 0.5% was prepared. Regarding the polymer aqueous solution, the viscosity of the polymer aqueous solution after 5 minutes was measured in a condition of a temperature of 25° C. and a rotation rate of 60 rpm, by using a B-type viscometer (manufactured by Toki Sangyo Co., Ltd.).

(Measurement of 0.5% Salt Viscosity)

2.5 g of a sample was dissolved in a sodium chloride aqueous solution of 4%, and thus, 500 g of a polymer aqueous solution of 0.5% was prepared. Regarding the polymer aqueous solution, the salt viscosity of the polymer aqueous solution after 5 minutes was measured in a condition of a temperature of 25° C. and a rotation rate of 60 rpm, by using a B-type viscometer (manufactured by Toki Sangyo Co., Ltd.).

(Measurement of 0.5% Insoluble Content)

The total amount (500 g) of the polymer aqueous solution of 0.5%, obtained in advance was filtered through a 80-mesh sieve having a diameter of 20 cm, the moisture was wiped off, and the insoluble content remaining on the sieve was collected, and thus, the mass of the insoluble content was measured by using an electronic balance (manufactured by SHINKO DENSHI CO., LTD.).

Synthesis Example 1

10.0 g of allyl bromide and 40.0 g of tetrahydrofuran (THF) were put into a beaker of 100 mL, and thus, a THF solution of allyl bromide was obtained. The obtained THF solution of allyl bromide was transfused into a dropping funnel of 100 mL. Next, 10.85 g of dimethyl aminopropyl acrylamide (DMPAA) and 40.0 g of tetrahydrofuran (THF) were put into an eggplant flask of 200 mL, and thus, a THF solution of DMPAA was obtained.

Further, the THF solution of allyl bromide was dropped into the THF solution of DMPAA for 20 minutes while stirring the THF solution of DMPAA with a magnetic stirrer, and was stirred for 2 hours after the dropping was ended, and thus, a precipitate was obtained. After the stirring was ended, standing still was performed for 12 hours, and the supernatant was removed, and then, decantation was performed in 200 mL of THF.

After that, the obtained precipitate was dried under reduced pressure, and thus, a white to pale yellow cross-linkable monomer (a) was obtained.

Synthesis Example 2

The same operation as that of Synthesis Example 1 was performed except that 10.85 g of dimethyl aminopropyl acrylamide was changed to 9.95 g of dimethyl aminoethyl acrylate (DMEA), and thus, a cross-linkable monomer (a) was obtained.

[Test 1: Production of Polymer Flocculant]

A polymer flocculant of each of the examples and each of the comparative examples was produced according to the following method. In addition, the abbreviations of a water-soluble unsaturated monomer and a copolymerizable monomer component in Table 1 and the following description, are as follows.

AAm: Acrylamide (manufactured by Wako Pure Chemical Industries, Ltd.)

DME: Methyl Chloride Salt of N'-N'-Dimethyl Aminoethyl Acrylate (manufactured by Osaka Organic Chemical Industry Ltd.)

MBAAM: Methylene Bisacrylamide (manufactured by Tokyo Chemical Industry Co., Ltd.)

Example 1-1

250 g of AAm and 0.025 g of a cross-linkable monomer (III-1) were put into a brown bottle of 1000 mL, and distilled water was added such that the total monomer concentration was set to 50%, and the total mass was set to 500 g, and thus, a monomer reaction liquid (AAm/Cross-Linkable Monomer (III-1)=99.99/0.01(%)) was prepared.

Further, DAROCUR-1173 (hereinafter, simply referred to as "D-1173") (manufactured by Ciba Specialty Chemicals) as a photoinitiator, and a hypophosphorous acid (hereinafter, simply referred to as "HPA") (manufactured by KANTO CHEMICAL CO., INC.) as a chain transfer agent, were put into the monomer reaction liquid such that the amounts were respectively set to 100 ppm and 50 ppm with respect to the total mass of the monomer reaction liquid, and a solution temperature was adjusted to 25° C. while blowing nitrogen gas for 15 minutes. After that, the monomer reaction liquid was transferred to a stainless steel reaction vessel, was irradiated with a chemical lamp having irradiation intensity of 0.2 W/m$^2$ for 20 minutes, and thus, polymerization was performed. Accordingly, a hydrogel-like polymer was obtained.

The hydrogel-like polymer was taken out from the vessel, and was crushed by using a small meat chopper. The crushed hydrogel-like polymer was dried at temperature of 70° C. for 16 hours, and then, was pulverized, and thus, a powder-like polymer (A-1) was obtained.

Example 1-2

The same operation as that of Example 1-1 was performed except that the amount of HPA was changed to 100 ppm.

Example 1-3

The same operation as that of Example 1-1 was performed except that the amount of HPA was changed to 200 ppm.

Example 1-4

The same operation as that of Example 1-3 was performed except that the amount of HPA was changed to 500 ppm, and the amount of the cross-linkable monomer (III-1) to be put was changed to 0.050 g (AAm/Cross-Linkable Monomer (III-1)=99.985/0.02(%)).

Example 1-5

The same operation as that of Example 1-3 was performed except that the cross-linkable monomer (III-1) was changed to a cross-linkable monomer (III-5).

Example 1-6

55 g of AAm, 387.5 g of a DME aqueous solution of 80 wt %, and 0.01 g of the cross-linkable monomer (III-1) were put into a brown bottle of 1000 mL, distilled water was added such that the total monomer concentration was set to 73%, and the total mass was set to 500 g, and thus, a monomer reaction liquid (AAm/DME/Cross-Linkable Monomer (III-1)=15.067/84.930/0.003(%)) was prepared.

Further, D-1173 as a photoinitiator, and a hypophosphorous acid as a chain transfer agent, were put into the monomer reaction liquid such that the amounts were respectively set to 20 ppm and 20 ppm with respect to the total mass of the monomer reaction liquid, and a solution temperature was adjusted to 25° C. while blowing nitrogen gas for 15 minutes.

After that, the monomer reaction liquid was transferred to a stainless steel reaction vessel, was irradiated with a chemical lamp having irradiation intensity of 0.2 W/m$^2$ for 20 minutes, and thus, polymerization was performed. Accordingly, a hydrogel-like polymer was obtained.

The hydrogel-like polymer was taken out from the vessel, and was crushed by using a small meat chopper. The crushed hydrogel-like polymer was dried at a temperature of 70° C. for 16 hours, and then, was pulverized, and thus, a powder-like polymer (A-2) was obtained.

Example 1-7

55 g of AAm, 387.5 g of a DME aqueous solution of 80 wt %, and 0.045 g of the cross-linkable monomer (III-1) were put into a brown bottle of 1000 mL, and distilled water was added such that the total monomer concentration was set to 73%, and the total mass was set to 500 g, and thus, a monomer reaction liquid (AAm/DME/Cross-Linkable Monomer (III-1)=15.066/84.921/0.013(%)) was prepared.

Further, D-1173 as a photoinitiator, and HPA as a chain transfer agent were put into the monomer reaction liquid such that the amounts were respectively set to 130 ppm and 50 ppm with respect to the total mass of the monomer reaction liquid, and a solution temperature was adjusted to 25° C. while blowing nitrogen gas for 15 minutes.

Comparative Example 1-1

A polymer (B-1) was obtained by performing the same operation as that of Example 1-1, except that the cross-linkable monomer (III-1) was not used.

Comparative Example 1-2

The same operation as that of Example 1-1 was performed except that the cross-linkable monomer (III-1) was changed to MBAAM (AAm/MBAAM=99.99/0.01).

Comparative Example 1-3

The same operation as that of Comparative Example 1-2 was performed except that the amount of HPA was changed to 100 ppm.

Comparative Example 1-4

The same operation as that of Comparative Example 1-2 was performed except that the amount of HPA was changed to 200 ppm.

Comparative Example 1-5

A polymer (B-2) was obtained by performing the same operation as that of Example 1-6, except that the cross-linkable monomer (III-1) was not used, the water-soluble unsaturated monomer was changed to only AAm and a DME aqueous solution of 80 wt %, and the amount of HPA was changed to 26 ppm.

In each of the (co)polymers obtained in Examples 1-1 to 1-7 and Comparative Examples 1-1 to 1-5, a 0.5% viscosity, a 0.5% salt viscosity, and a 0.5% insoluble content were measured. The results are shown in Table 1.

TABLE 1

|  | Water-Soluble Unsaturated Monomer | Cross-Linkable Monomer | Concentration of Cross-Linkable Monomer (ppm) | Amount of HPA (ppm) | Concentration of D-1173 (ppm) | 0.5% Viscosity (mPa · s) | 0.5% Salt Viscosity (mPa · s) | 0.5% Insoluble Content (g) |
|---|---|---|---|---|---|---|---|---|
| Example 1-1 (Polymer A-1) | AAm | Cross-Linkable Monomer (III-1) | 100 | 50 | 100 | 10.0 | 24.1 | 0.2 |

TABLE 1-continued

| | Water-Soluble Unsaturated Monomer | Cross-Linkable Monomer | Concentration of Cross-Linkable Monomer (ppm) | Amount of HPA (ppm) | Concentration of D-1173 (ppm) | 0.5% Viscosity (mPa·s) | 0.5% Salt Viscosity (mPa·s) | 0.5% Insoluble Content (g) |
|---|---|---|---|---|---|---|---|---|
| Example 1-2 | AAm | Cross-Linkable Monomer (III-1) | 100 | 100 | 100 | 9.1 | 14.9 | 0.3 |
| Example 1-3 | AAm | Cross-Linkable Monomer (III-1) | 100 | 200 | 100 | 9.5 | 10.9 | 0 |
| Example 1-4 | AAm | Cross-Linkable Monomer (III-1) | 500 | 200 | 100 | 8.8 | 10.4 | 0.6 |
| Example 1-5 | AAm | Cross-Linkable Monomer (III-5) | 100 | 200 | 100 | 8.3 | 9.8 | 0.1 |
| Example 1-6 (Polymer A-2) | AAm/DME | Cross-Linkable Monomer (III-1) | 30 | 20 | 20 | 3060 | 53 | 20 |
| Example 1-7 | AAm/DME | Cross-Linkable Monomer (III-1) | 130 | 50 | 130 | 2820 | 39 | 20 |
| Comparative Example 1-1 (Polymer B-1) | AAm | — | — | 50 | | 14.4 | 24 | 0 |
| Comparative Example 1-2 | AAm | MBAAM | 100 | 50 | | 31.3 | — | 117.5 |
| Comparative Example 1-3 | AAm | MBAAM | 100 | 100 | | 59.4 | — | 135.6 |
| Comparative Example 1-4 | AAm | MBAAM | 100 | 200 | | 15.9 | — | 128.9 |
| Comparative Example 1-5 (Polymer B-2) | AAm/DME | — | — | 26 | 20 | 2570 | 40 | 0 |

※ AAm: Acrylamide
※ DMPAA-Allyl: Synthesized Cross-Linking Agent
※ MBAAM: Commercially Available Cross-Linking Agent

[Test 2: Sludge Treatment]

A kaolinite aqueous solution of 3% was prepared as a model sample of sludge, and 300 mL of digestive sludge was sampled into a beaker of 500 mL. Next, the polymer of the type shown in Table 2, was formed into a polymer aqueous solution of 0.3% by distilled water, and the polymer aqueous solution was added to the digestive sludge by the added amount shown in Table 2. Next, a flock was generated by stirring the digestive sludge for 30 seconds with a metal spatula, and the flock was filtered by a sieve with a mesh of 2 mm square, and thus, it was determined that a grain diameter of a flock which passed through the mesh, was less than 2 mm, and a grain diameter of a flock which did not pass through the mesh, was greater than or equal to 2 mm. In addition, a settling time of the flock was determined. The grain diameter and the settling time of the flock are shown in Table 2.

TABLE 2

| | Polymer | Added Amount (ppm) | Flock Grain Diameter (mm) | Settling Time (second) |
|---|---|---|---|---|
| Example 2-1 | A-1 | 160 | Greater than or equal to 2 mm | 14 |
| Comparative Example 2-1 | B-1 | 160 | Less than 2 mm | 21 |

Model Sludge: Kaolinite Aqueous Solution of 3%
Added Amount of Flocculant: 160 ppm Further, digestive sludge of a certain sewage treatment plant was prepared as a sample of the sludge, and 300 mL of the digestive sludge was sampled into a beaker of 500 mL. Next, the polymer of the type shown in Table 3, was formed into a polymer aqueous solution of 0.5% by distilled water, and the polymer aqueous solution was added to the digestive sludge by the added amount shown in Table 3. Next, a flock was generated by stirring the digestive sludge for 30 seconds with a metal spatula, and the flock was filtered by a sieve with a mesh of 15 mm square, and thus, it was determined that a grain diameter of a flock which passed through the mesh, was less than 15 mm, and a grain diameter of a flock which did not pass through the mesh, was greater than or equal to 15 m.

In addition, a flock strength was determined as follows. The grain diameter and the strength of the flock are shown in Table 3.

(Flock Strength)
A. In a case where the flock is crushed with hands, an elastic force to rebound is felt.
B: In a case where the flock is crushed with hands, the flock does not rebound, and the elastic force is not felt.

TABLE 3

| | Polymer | Added Amount (ppm) | Flock Grain Diameter (mm) | Flock Strength |
|---|---|---|---|---|
| Example 2-2 | A-2 | 160 | Greater than or equal to 15 mm | A |
| Comparative Example 2-2 | B-2 | 160 | Less than 15 mm | B |

Sludge: N Sewage Treatment Plant
Added Amount of Flocculant: 160 ppm

From Table 1, it was known that a polymer with less insoluble content of 0.5% was able to be obtained by using the cross-linkable monomer (a). On the other hand, it was known that a polymer having a high 0.5% insoluble content was obtained in a case of using MBAAM.

Further, as it is obvious from Table 2, in a case where the model sludge was subjected to a flocculation treatment by using the polymer obtained in Example 1-1 (Example 2-1), a grain diameter of a flock to be obtained was large, a settling time was fast, and drainage was excellent.

In addition, as it is obvious from Table 3, in a case where the actual sludge was subjected to the flocculation treatment by using the polymer obtained in Example 1-6 (Example 2-2), a grain diameter of a flock to be obtained was large, and a strength was also high. Accordingly, it was confirmed that the polymer obtained in Example 1-1 and Example 1-6, was excellent in the flocculation performance.

On the other hand, in the case of using the polymer obtained in Comparative Example 1-1 (Comparative Example 2-1), a grain diameter of a flock was small, a settling rate was slow, and drainage was poor, compared to the examples. Further, in the case of using the polymer obtained in Comparative Example 1-5 (Comparative Example 2-2), a grain diameter of a flock was small, and a strength was also low, compared to the examples. Accordingly, the polymer obtained in Comparative Example 1-1, was not excellent in the flocculation performance, compared to the examples.

Next, the invention will be described in detail by the example, as a paper strengthening agent application.

Furthermore, in the examples and the comparative examples, measured values of a 15% viscosity and a molecular weight, were obtained by performing measurement with respect to a powder-like paper strengthening agent, according to the following method.

(Measurement of 15% Viscosity)

15 g of a sample was dissolved in water, and thus, 100 g of a polymer aqueous solution of 15% was prepared. Regarding the polymer aqueous solution, the viscosity of the polymer aqueous solution after 5 minutes was measured in a condition of a temperature of 25° C. and a rotation rate of 3 rpm, by using a B-type viscometer (manufactured by Toki Sangyo Co., Ltd.).

(Measurement of Weight Average Molecular Weight)

0.05 g of a sample was dissolved in water, and thus, 20 g of a polymer aqueous solution of 0.5% was prepared. Next, the polymer aqueous solution was dissolved in an aqueous solution in which sodium chloride and an acetic acid were respectively 0.5 mol/l, and thus, a polymer aqueous solution of 0.1% was prepared.

A weight average molecular weight Mw was measured by using the polymer aqueous solution, with GPC (manufactured by SHIMADZU CORPORATION). Furthermore, the measurement was performed at a flow rate of 0.5 ml/min, by using pullulan as a standard substance.

[Test 3: Production of Polymer Paper Strengthening Agent]

A polymer paper strengthening agent of each of the examples and each of the comparative examples was produced according to the following method. In addition, the abbreviations of a water-soluble unsaturated monomer and a copolymerizable monomer component in Table 4 and the following description, are as follows.

AAm: Acrylamide (manufactured by Wako Pure Chemical Industries, Ltd.)

DM: N'-N'-Dimethyl Aminoethyl Methacrylate (manufactured by Tokyo Chemical Industry Co., Ltd.)

IA: Itaconic Acid (manufactured by Wako Pure Chemical Industries, Ltd.)

Example 3-1

176.6 g of AAm, 16.6 g of DM, 6.8 g of IA, and 0.5 g of the cross-linkable monomer (III-1) were put into a brown bottle of 1000 mL, and distilled water was added such that the total monomer concentration was set to 40%, and the total mass was set to 500 g, and thus, a monomer reaction liquid (AAm/DM/IA/Cross-Linkable Monomer (III-1)= 88.08/8.28/3.39/0.25(%)) was prepared.

Further, D-1173 as a photoinitiator, and a hypophosphorous acid as a chain transfer agent, were put into the monomer reaction liquid such that the amounts were respectively set to 20 ppm and 1000 ppm with respect to the total mass of the monomer reaction liquid, and a solution temperature was adjusted to 25° C. while blowing nitrogen gas for 15 minutes.

After that, the monomer reaction liquid was transferred to a stainless steel reaction vessel, and was irradiated with a chemical lamp having irradiation intensity of 0.2 W/m$^2$ for 20 minutes, and thus, polymerization was performed. Accordingly, a hydrogel-like polymer was obtained.

The hydrogel-like polymer was taken out from the vessel, and was crushed by using a small meat chopper. The crushed hydrogel-like polymer was dried at a temperature of 70° C. for 16 hours, and then, was pulverized, and thus, a powder-like polymer (C-1) was obtained.

Comparative Example 3-1

A polymer (C-2) was obtained by performing the same operation as that of Example 3-1, except that the cross-linkable monomer (III-1) was changed to only AAm, DM, and IA.

In each of the (co)polymers obtained in Example 3-1 and Comparative Example 3-1, a 15% viscosity and a weight average molecular weight were measured. The results are shown in Table 4.

TABLE 4

| | Water-Soluble Unsaturated Monomer | Cross-Linkable Monomer | Concentration of Cross-Linkable Monomer (ppm) | Amount of HPA (ppm) | Concentration of D-1173 (ppm) | 15% Viscosity (mPa · s) | Weight Average Molecular Weight (Mw) |
|---|---|---|---|---|---|---|---|
| Example 3-1 (Polymer C-1) | AAm/DME/IA | Cross-Linkable Monomer (III-1) | 2500 | 1000 | 20 | 33,780 | 1425000 |
| Comparative Example 3-1 (Polymer C-2) | AAm/DME/IA | — | 2500 | 1000 | 20 | 52,600 | 1251000 |

[Test 3: Measurement of Paper Strength]

1000 ppm of a 0.5% aqueous solution of a polymer C-1 with respect to the total amount, was added while stirring a waste corrugated fiberboard of CSF480 in 868.4 g of slurry of 0.8%, and the stirring was continuously performed for 20 seconds. After that, papermaking was performed by using the obtained pulp slurry, in a square sheet machine. A wet sheet subjected to the papermaking, was dried at 110° C. for 3 minutes in a drum dryer, and thus, handmade paper having a basis weight of 125 g/m², was obtained. The obtained dry paper was subjected to humidity conditioning for 24 hours in a constant temperature and humidity room of 20° C. and RH65%, and then, a specific burst strength (JIS-P8112) was measured. The same operation was performed with respect to a polymer C-2. The results are shown in Table 5.

TABLE 5

|  | Polymer | Specific Burst Strength (kPa · m²/g) |
|---|---|---|
| Example 4-1 | C-1 | 2.84 |
| Comparative Example 4-2 | C-2 | 2.64 |

From Table 4, it was known that a polymer having a low 15% viscosity was obtained by using the cross-linkable monomer (III-1), despite the same value of the weight average molecular weight. Further, as it is obvious from Table 5, in a case where the polymer C-1 obtained in Example 3-1 was added at the time of performing the papermaking, and a paper strength was measured (Example 4-1), it was known that a specific burst strength became higher. Accordingly, it was confirmed that the polymer obtained in Example 3-1, was excellent in the paper strength improving performance.

On the other hand, in the case of using the polymer C-2 obtained in Comparative Example 3-1 (Comparative Example 4-2), a specific burst strength became lower, compared to the examples. Accordingly, the polymer obtained in Comparative Example 3-1, was not excellent in the paper strength improving performance, compared to the examples.

INDUSTRIAL APPLICABILITY

Hereinbefore, as described above in detail, according to the invention, it is possible to prepare a polymer flocculant which is capable of generating a coarse flock, is capable of controlling the structure of the polymer with a general aqueous solution polymerization method, and is excellent in water-solubility and water dispersibility, with a branched or cross-linking structure, by using two or more types of different cross-linkable monomers. In addition, it is possible to prepare a paper strengthening agent which is excellent in a specific burst strength.

The invention claimed is:

1. A copolymer, comprising, in polymerized form:
a cross-linkable monomer (a) of formula (II),

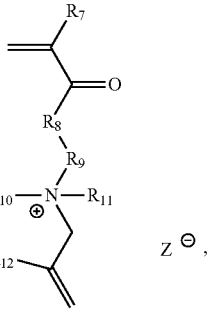

(II)

$R_{10}$ and $R_{11}$ independently being a linear or branched alkyl group comprising 1 to 6 carbon atoms, $R_7$ being H or a methyl group, $R_8$ being O or NH, $R_9$ being $C_nH_{2n}$ with n being in a range of 1 to 6, $R_{12}$ being H, a methyl group, or an alkyl ester group having a linear, branched, or cyclic structure comprising 1 to 6 carbon atoms, and Z is a chlorine ion, a bromine ion, or an iodine ion; and
a water-soluble unsaturated monomer (b) having a polymerizable unsaturated bond in the molecule,
wherein, in the copolymer, units from the monomer (a) are in a range of from 0.001 to 1.0% by mass with respect to 100% by mass of units from the monomer (b), and
wherein, when a viscosity of the copolymer is measured by a rotatory viscometer, at a temperature of 25° C. and a rotation rate of 60 rpm, as an aqueous solution of 0.5 mass %, the viscosity is greater than or equal to 5 mPa·s and less than or equal to 10000 mPa·s.

2. A polymer flocculant, comprising:
the copolymer of claim 1.

3. A paper strengthening agent, comprising:
the copolymer of claim 1.

4. A method for producing a polymer flocculant including the copolymer of claim 1, the method comprising:
dissolving the cross-linkable monomer (a) and the water-soluble unsaturated monomer (b) in water; and
polymerizing the cross-linkable monomer (a) and the water-soluble unsaturated monomer (b) dissolved in water in a homogeneous system.

5. The copolymer of claim 1, wherein the cross-linkable monomer (a) of formula (II) comprises

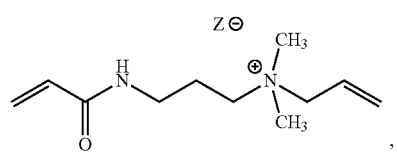

wherein Z is chloride and/or bromide.

6. The copolymer of claim 1, wherein the cross-linkable monomer (a) of formula (II) comprises

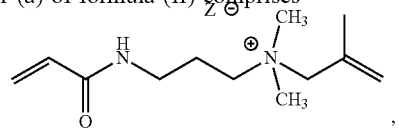

wherein Z is chloride and/or bromide.

7. The copolymer of claim 1, wherein the cross-linkable monomer (a) of formula (II) comprises

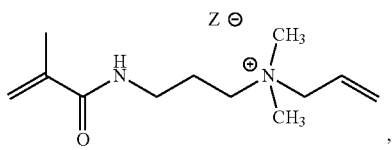

wherein Z is chloride and/or bromide.

8. The copolymer of claim 1, wherein the cross-linkable monomer (a) of formula (II) comprises

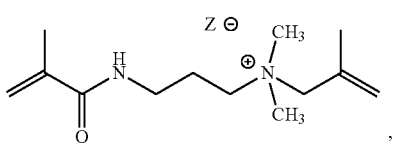

wherein Z is chloride and/or bromide.

9. The copolymer of claim 1, wherein the cross-linkable monomer (a) of formula (II) comprises

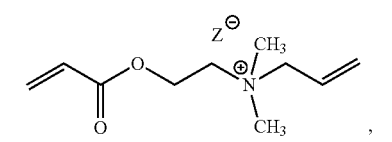

wherein Z is chloride and/or bromide.

10. The copolymer of claim 1, wherein the cross-linkable monomer (a) of formula (II) comprises

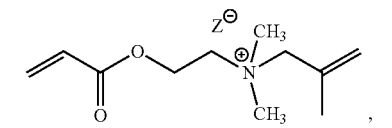

wherein Z is chloride and/or bromide.

11. The copolymer of claim 1, wherein the cross-linkable monomer (a) of formula (II) comprises

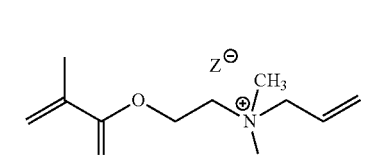

wherein Z is chloride and/or bromide.

12. The copolymer of claim 1, wherein the cross-linkable monomer (a) of formula (II) comprises

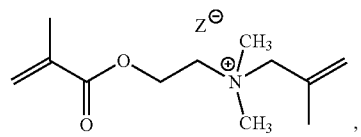

wherein Z is chloride and/or bromide.

13. The copolymer of claim 1, wherein the cross-linkable monomer (a) of formula (II) comprises

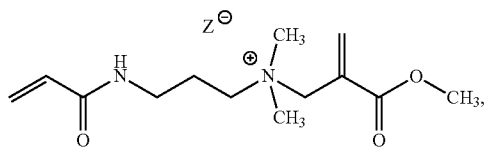

wherein Z is chloride and/or bromide.

14. The copolymer of claim 1, wherein the cross-linkable monomer (a) of formula (II) comprises

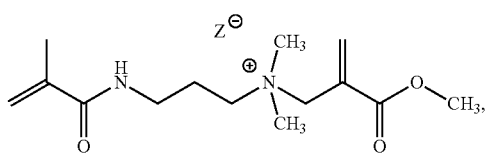

wherein Z is chloride and/or bromide.

15. The copolymer of claim 1, wherein the cross-linkable monomer (a) of formula (II) comprises

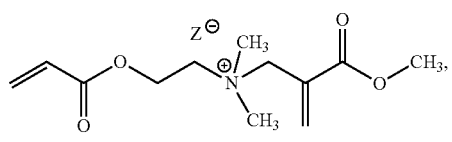

wherein Z is chloride and/or bromide.

16. The copolymer of claim 1, wherein the cross-linkable monomer (a) of formula (II) comprises

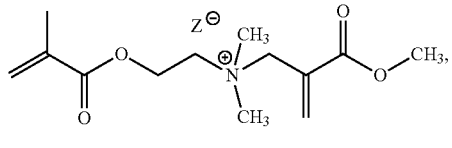

wherein Z is chloride and/or bromide.

17. A copolymer, comprising, in polymerized form: a cross-linkable monomer (a) of a formula

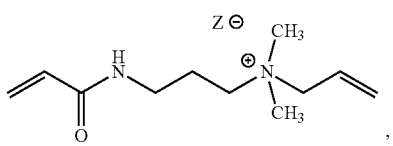

wherein Z is chloride and/or bromide; and
a water-soluble unsaturated monomer (b) having a polymerizable unsaturated bond in the molecule,
wherein, in the copolymer, units from the monomer (a) are in a range of from 0.001 to 1.0% by mass with respect to 100% by mass of units from the monomer (b).

18. A polymer flocculant, comprising:
the copolymer of claim 17.

19. A paper strengthening agent, comprising:
the copolymer of claim 17.

* * * * *